United States Patent [19]

Crawford et al.

[11] Patent Number: 5,340,889
[45] Date of Patent: Aug. 23, 1994

[54] LIQUIFICATION OF BIS-CARBONATES OF BIS-GLYCIDYL ETHERS

[75] Inventors: Wheeler C. Crawford, Houston; Edward T. Marquis, Austin; Howard P. Klein, Katy, all of Tex.

[73] Assignee: Texaco Chemical Company, White Plains, N.Y.

[21] Appl. No.: 93,568

[22] Filed: Jul. 19, 1993

[51] Int. Cl.$^5$ .................. C08G 64/00; C07C 261/00; C07C 269/00; C07C 271/00
[52] U.S. Cl. ...................... 525/523; 528/111; 528/370; 549/230; 549/229; 560/25; 560/26; 560/115; 560/158
[58] Field of Search ............... 525/523; 528/370, 111; 549/230, 229; 560/25, 26, 115, 158

[56] References Cited

U.S. PATENT DOCUMENTS

| | | | |
|---|---|---|---|
| 2,802,022 | 8/1957 | Grozos et al. | 260/471 |
| 2,935,494 | 5/1960 | Whelan et al. | 260/77.5 |
| 3,072,613 | 1/1963 | Whelan et al. | 260/77.5 |
| 3,084,140 | 4/1963 | Gurgiolo et al. | 525/403 |
| 3,624,016 | 11/1971 | Lew | 528/266 |
| 4,892,954 | 1/1990 | Brindopke et al. | 549/230 |
| 5,175,231 | 12/1992 | Rappaport et al. | 528/106 |

FOREIGN PATENT DOCUMENTS

| | | |
|---|---|---|
| 413824A | 12/1969 | U.S.S.R. . |
| 351835 | 10/1972 | U.S.S.R. . |
| 359255 | 1/1973 | U.S.S.R. . |
| 1495555 | 12/1977 | United Kingdom . |

*Primary Examiner*—Frederick Krass
*Attorney, Agent, or Firm*—Russell R. Stolle; Walter D. Hunter

[57] ABSTRACT

Liquid hydroxyurethane products having cyclocarbonate end groups are prepared by reacting a molar excess of a bis-carbonate of a bis-glycidyl ether of neopentyl glycol or 1,4-cyclohexanedimethanol with a polyoxyalkylenediamine such as a polyoxypropylenediamine. These products are useful for the preparation of polyurethanes, polyurethane polyols, polyester polyurethane polyols, and polycarbonate polyurethane polyols.

14 Claims, No Drawings

LIQUIFICATION OF BIS-CARBONATES OF BIS-GLYCIDYL ETHERS

BACKGROUND OF THE INVENTION

1. Field of the Invention

This invention relates to liquid hydroxyurethane products of bis-carbonates of bis-glycidyl ethers and to a process for their preparation. More particularly, this invention relates to liquid hydroxyurethanes having cyclocarbonate end groups products prepared by reacting a molar excess of a bis-carbonate of a bis-glycidyl ether with a difunctional diamine such as a polyoxypropylenediamine.

Bis-carbonates of bis-glycidyl ethers, which are materials known in the art, have been suggested for use in preparing urethane materials, polyurethane polyols, polyester polyurethane polyols, polyether polyurethane polyols, polycarbonate polyurethane polyols and as additives for curing agent formulations such as those utilized for curing of epoxy resins. Because some of these bis-carbonates of bis-glycidyl ethers are solid-liquid mixtures, i.e., i.e., two phase materials, they are not satisfactory for mixing with the usual liquid formulations employed, for example, in the curing of epoxy resins. The bis-carbonates prepared from the bis-glycidyl ether of 1,4-cyclohexanedimethanol and from the bis-glycidyl ether of neopentyl glycol are mainly solid at room temperature and at 60° C. the bis-carbonate of the bis-glycidyl ether of 1,4-cyclohexanedimethanol is about one-half solid and one-half liquid while the bis-carbonate of the bis-glycidyl ether of neopentyl glycol is about three-quarters liquid and about one-quarter solid.

The invention of this application relates to the reaction of a molar excess of these liquid-solid materials with a polyoxypropylenediamine to yield hydroxyurethane products which contain active carbonate groups and which are single phase, single layered, viscous liquids at room temperature. Thus, by the process of this invention these bis-carbonates surprisingly are converted from troublesome, liquid-solid materials to viscous liquids containing no solids which are generally clear, single phase, single layered liquids.

2. Prior Art

U.S. Pat. No. 5,175,231 to Rappoport et al., teaches a method for preparing a urethane by reacting a compound containing a plurality of cyclocarbonate groups with a diamine in which the two amine groups have different reactivities with cyclocarbonate so as to form a urethane oligomer with amine end groups. The urethane oligomer can then be reacted in different ways to form a polyurethane.

United Kingdom Patent No. 1,495,555 to Petrov et al. (December, 1977), discloses a method for producing a polyurethane by reacting a hydrocarbon polymer having at least one double bond such as cis-1,4-polyisoprene, polybutadiene, etc. with a primary or secondary amine, such as benzylamine, xylylene diamine, etc. These products which have a wide range of uses, e.g., shoes, tires, adhesives and coatings, have good strength, elasticity, abrasion resistance, dynamic properties, resistance to low temperatures and bond strongly to metals.

U.S.S.R. Inventor's Certificate No. 359,255 to Petrov et al. (Jan. 11, 1973), discloses the preparation of polyurethanes by the reaction of oligomer diamines such as oligomer diamine diurethane formed by reacting polyoxypropylene dicarbonate with xylenediamine and then in a second step reacting oligomer diamine with tricyclocarbonate based on trimethylolpropane triglycidyl ether to form a cross-linked urethane elastomer.

U.S.S.R. Inventor's Certificate No. 351,835 to Shapiro et al. (Oct. 19, 1972), teaches a process for preparing polyesters suitable for use in the synthesis of polyurethanes by reaction of a diglycidyl compound, such as ethylene glycol diglycidyl ether and carbon dioxide in the presence of a tetraalkylammonium halide.

U.S.S.R. Inventor's Certificate No. 413,824A to Petrov et al. (Dec. 24, 1969), discloses a process for preparing polymer materials with a urethane group in the chain by reaction of an epoxy resin with a polyamine containing urethane groups which are obtained by the reaction of a primary or secondary diamine with bicyclic carbonates.

U.S. Pat. No. 2,802,022 to Grozos discloses a process for preparing polyurethanes in which a hydroxy carbonate formed by reacting a cyclic carbonate with, for example, a polyamine and in a second step reacting the hydroxyl carbonate with urea to form the corresponding polyurethane.

U.S. Pat. No. 3,072,613 to Whelan, Jr., et al., teaches the preparation of resinous polyurethane products by the reaction of a multiple cyclic carbonate and polyfunctional aliphatic amines having a plurality of reactive amine groups. These polymeric substances are readily cast into tough, colorless films having excellent clarity and tear resistance by extrusion or solvent casting techniques.

U.S. Pat. No. 2,935,494 to Whelan, Jr. teaches a process for the preparation of polymeric compositions from erythritol dicarbonate and polyfunctional aliphatic amines having a plurality of reactive amine groups such as unhindered primary aliphatic diamines as exemplified by ethylene diamine, hexamethylene diamine, etc.

SUMMARY OF THE INVENTION

The liquid hydroxyurethane products of this invention which have cyclocarbonate end groups are prepared by reacting a polyoxyalkylenediamine with a molar excess of a bis-carbonate of a bis-glycidyl ether of the formula:

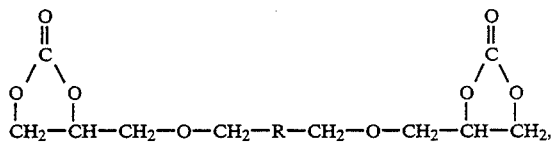

wherein R is selected from the group consisting of:

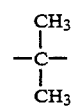

and

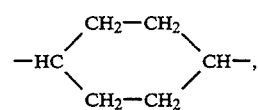

In conducting the reaction the molar ratio of the bis-carbonate material reacted with the polyoxyalkylenediamine will range from 5.0:1 to about 2.0:1, preferably will be from about 3.5:1 to about 2.0:1.

The products formed by the reaction of the bis-carbonate of the bis-glycidyl ether with the polyoxyalkylenediamine in the process of this invention have cyclocarbonate end groups and have the formula:

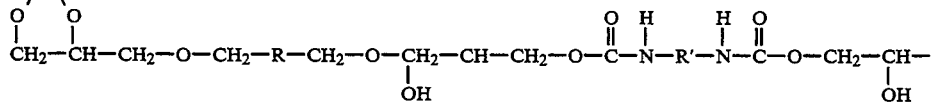

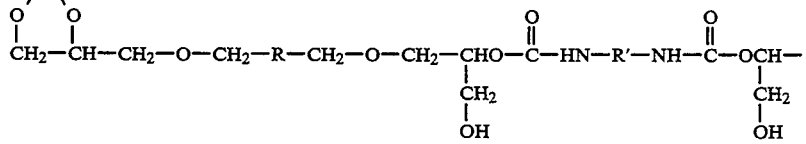

wherein R is selected from the group consisting of:

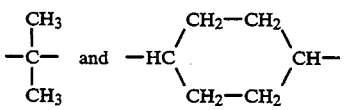

and R' is

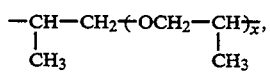

where x ranges from 2 to about 60.

The advantage of this process is that with it potentially valuable products, i.e., bis-carbonates of bis-glycidyl ethers, are converted to viscous, single-layered, single phase liquids instead of solid-liquid mixtures present in the original products.

DESCRIPTION OF THE PREFERRED EMBODIMENTS

Preparation of the Bis-Carbonates of the Bis-Glycidyl Ethers

The bis-glycidyl ethers of neopentyl glycol and 1,4-cyclohexanedimethanol were converted to the corresponding bis-carbonates which are employed as starting materials in the process of this invention in nearly theoretical yield by carbonation reaction with carbon dioxide in the presence of tetraethylammonium bromide (TEAB) at 180° C. The carbonation reaction proceeds as follows where for purposes of illustration the reaction between the bis-glycidyl ether of neopentyl glycol and carbon dioxide is shown:

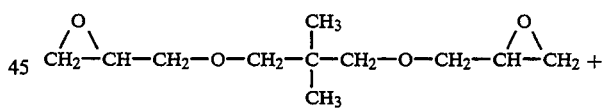

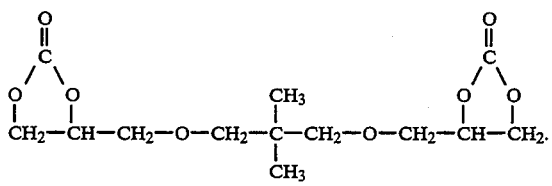

As previously pointed out, in preparing the liquid hydroxyurethane products of this invention the bis-carbonate of the bis-glycidyl ether is reacted with the polyoxyalkylenediamine in a molar ratio of the bis-carbonate of the bis-glycidyl ether to the polyoxyalkylenediamine of from 5.0:1 to about 2.0:1.

In the process of this invention a typical hydroxyurethane prepolymer formed, for example, by the reaction of the bis-carbonate of the bis-glycidyl ether of neopentyl glycol and the polyoxyalkylenediamine has the formula:

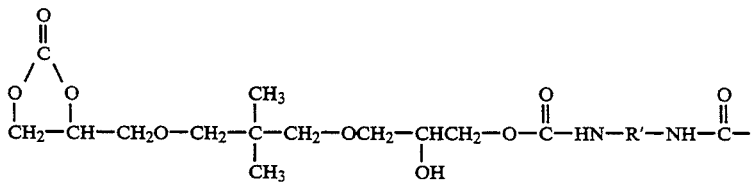

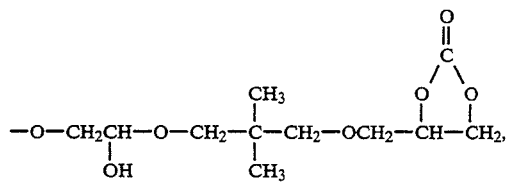

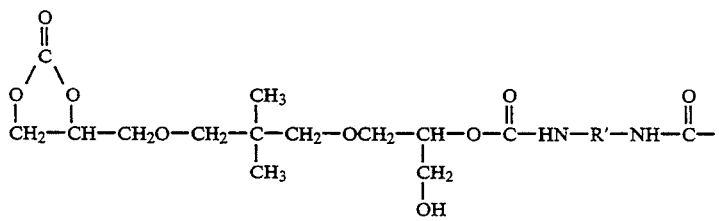

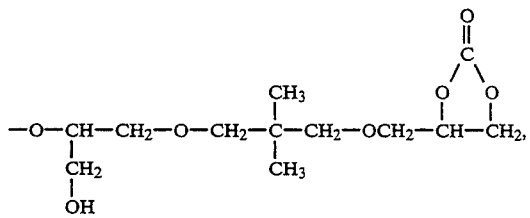

where R' is a polyoxyalkylene group.

Useful polyoxyalkylenediamines which can be reacted with bis-carbonates of the previously described bis-glycidyl ethers to form the liquid reaction products of this invention include polyoxyalkylenediamines having molecular weights ranging from about 200 to about 4000 and, preferably, polyoxypropylenediamines of the JEFFAMINE ® D series, as exemplified by but not limited to:

JEFFAMINE ® D-230 having the formula:

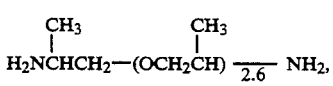

JEFFAMINE ® D-400 having the formula:

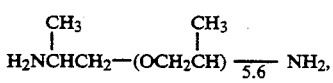

JEFFAMINE ® D-2000 having the formula:

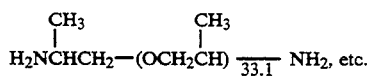

All of the above JEFFAMINE ® polyoxyalkylenediamine products are marketed by Texaco Chemical Company, Houston, Tex. The numerical designation of these products indicates the approximate molecular weight.

The preparation of polyoxyalkylenediamines suitable as reactants in the process of this invention is described in Yeakey U.S. Pat. No. 3,654,370 which is incorporated herein by reference in its entirety.

The process is conveniently conducted at temperatures ranging from ambient up to about 250° C. and at a pressure ranging from atmospheric up to about 3000 psig while atmospheric pressure is preferred.

The invention will be further illustrated by the following specific examples which are not to be considered as limiting the scope of this invention.

EXAMPLE 1

Preparation of the Bis-Carbonate of the Bis-Glycidyl Ether of Neopentyl Glycol (6860-85)

To a 1 liter stainless steel autoclave was added 400.0 grams (2.96 moles of epoxide) of the bis-glycidyl ether of neopentyl glycol (HELOXY ® 68 Epoxy Functional Modifier from Rhone Poulenc) and 5.0 grams of tetraethylammonium bromide catalyst. The clave was purged with carbon dioxide and sealed. Carbon dioxide (200.0 grams, 4.54 moles) was added to clave and the clave was heated to 180° C. with stirring and held at 180° C. for 2.0 hours. After cooling and venting the excess carbon dioxide, the product weighed 526.2 grams or 521.2 grams less the catalyst weight. The weight gain of $521.2-400.0=121$ compared well with a theoretical weight gain of 130.2 grams (2.9 moles of epoxide $\times 44 = 130.2$ g.). The product was heated to 80°-90° C. and filtered to remove solids (heavier carbonates, catalyst, etc.). Upon standing at room temperature, the product solidified with about one-half being solid, one-half remaining liquid. At 60° C. the product was about three-quarters liquid and one-quarter solid.

EXAMPLE 2

Preparation of the Bis-Carbonate of the Bis-Glycidyl Ether of Neopentyl Glycol (6860-86)

This run conducted identically to that described above in EXAMPLE 1, except the product weight was 522.3 g. The weight of product less the catalyst charged was 517.3 g. The product from the run was heated to 80°–90° C. and filtered to remove small quantities of solids. The weight gain in this run (117.3 g.) indicated a high conversion to carbonate. At room temperature and at 60° C. the filtered product was similar to the product from EXAMPLE 1 in terms of physical state.

EXAMPLE 3

Preparation of the Bis-Carbonate of the Bis-Glycidyl Ether of 1,4-Cyclohexanedimethanol (6860-93)

Using the procedure as described in EXAMPLE 1, 428.0 g. (2.68 moles of epoxide) of the bis-glycidyl ether of 1,4-cyclohexanedimethanol (HELOXY® 107 Epoxy Functional Modifier from Rhone Poulenc) and 5.0 grams of tetraethylammonium bromide were added to the 1 liter stainless steel autoclave. The clave was purged with carbon dioxide. Carbon dioxide (180.0 grams, 4.09 moles) was added to the clave and the clave was heated to 180° C. and held at 180° C. for 2.0 hours. After cooling and venting the excess carbon dioxide, the product weighed 547.2 grams or 542.2 grams less the catalyst charged. The weight gain of 114.2 grams compares favorably with the theoretical weight gain of 117.7 grams (2.675 moles of epoxide×44=117.7 g.). The product was filtered hot (82°–90° C.) to remove small quantities of solids. Upon standing at room temperature, the product solidified completely. At 60° C. the product was about one-half solid and one-half liquid.

EXAMPLE 4

Preparation of the Bis-Carbonate of the Bis-Glycidyl Ether of 1,4-Cyclohexanedimethanol (6860-92)

This example was conducted in the same manner as described in EXAMPLE 3. The recovered product, i.e., the bis-carbonate of the bis-glycidyl ether of 1,4-cyclohexanedimethanol weighed 546.5 g. or 541.4 g. (less weight of the catalyst), the weight gain of 113.4 grams compared favorably with the theoretical weight gain of 117.7 grams (2.675 mole epoxide×44=117.7 g.). The product workup was the same as in EXAMPLE 3 and again at room temperature the product was solid and at 60° C. the product was one-half solid and one-half liquid.

EXAMPLE 5

Liquid Product of the Bis-Carbonate of the Bis-Glycidyl Ether of 1,4-Cyclohexanedimethanol and JEFFAMINE® D-400 (6946-89)

To a 250 ml round-bottomed flask equipped with a mechanical stirrer, thermometer, dropping funnel, and nitrogen pad, were added 172.0 grams of the bis-carbonate of the bis-glycidyl ether of 1,4-cyclohexanedimethanol (6860-93 product from EXAMPLE 3), followed by the slow addition, via dropping funnel, of 40.0 grams of JEFFAMINE® amine polyoxypropylene diamine D-400. The reaction mixture was heated to about 70° C. for 1.0 hour, followed by 130° C. for 2.0 hours. The reaction mixture was cooled to 100° C. and held there for 1.0 hour at aspirator vacuum. The primary amine value on the product was 0.07 mg/grams. In this reaction the 172.0 grams of bis-carbonate was 0.5 moles of bis-carbonate or 1.0 mole of carbonate groups. The diamine added was 40.0 grams or 0.1 mole of diamine or 0.2 mole of amine group. The product contained approximately 0.8 mole of reactive carbonate groups. The product at room temperature was a clear, single phase, very viscous liquid and at 60° C. the product was a viscous, pourable liquid.

EXAMPLE 6

Liquid Product of the Bis-Carbonate of the Bis-Glycidyl Ether of 1,4-Cyclohexanedimethanol and JEFFAMINE® D-2000 (6946-96)

This example was conducted in the same manner as EXAMPLE 5 except that 43.0 grams of the bis-carbonate of the bis-glycidyl ether of 1,4-cyclohexanedimethanol was reacted with 100.0 grams of JEFFAMINE® D-2000 which afforded a clear, viscous, single phase product. In this reaction 0.125 mole of the bis-carbonate (0.250 mole of carbonate) was reacted with 0.05 mole of D-2000 diamine (0.10 mole of amine). The product contained about 0.15 mole of reactive carbonate.

EXAMPLE 7

Liquid Product of the Bis-Carbonate of the Bis-Glycidyl Ether of Neopentyl Glycol and JEFFAMINE® D-400 (6946-91)

In this example which was conducted in the same manner as EXAMPLE 6 except that 152.0 grams of the bis-carbonate of the bis-glycidyl ether of neopentyl glycol (6860-85, product from EXAMPLE 1) was reacted with 40.0 grams of D-400 to afford a clear, viscous, single phase product at room temperature. In this reaction 0.5 mole of bis-carbonate (1.0 mole of carbonate group) was treated with 0.1 mole of D-400 amine (0.2 mole of amine group). The product contained approximately 0.8 mole of reactive carbonate groups.

EXAMPLE 8

Liquid Product of the Bis-Carbonate of the Bis-Glycidyl Ether of Neopentyl Glycol and JEFFAMINE® D-2000 (6946-94)

In this example which was carried out in the same manner as EXAMPLE 5, 53.2 grams (0,175 mole) of the bis-carbonate of the bis-glycidyl ether of neopentyl glycol (6860-85 product from EXAMPLE 1) was reacted with 100 grams (0.05 mole) of JEFFAMINE® D-2000 to afford a clear, single phase, viscous liquid.

What is claimed is:

1. A liquid hydroxyurethane product having cyclocarbonate end groups prepared by reacting a bis-carbonate of a bis-glycidyl ether of the formula:

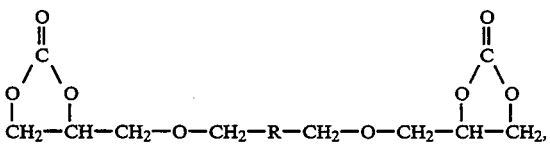

wherein R is selected from the group consisting of:

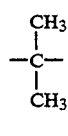

and

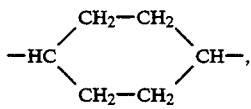

with a polyoxyalkylenediamine and wherein the molar ratio of the bis-carbonate of the bis-glycidyl ether reacted with the polyoxyalkylenediamine ranges from 5.0:1 to about 2.0:1 and wherein the polyoxyalkylenediamine is a polyoxypropylenediamine having the formula:

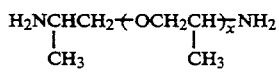

where x ranges from 2 to about 60.

2. The product of claim 1 wherein the reaction is conducted at a temperature ranging from ambient to about 250° C. and at a pressure ranging from atmospheric up to about 3000 psig.

3. The product of claim 1 wherein R is

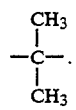

4. The product of claim 1 wherein R is

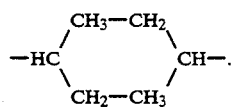

5. The product of claim 1 wherein in the polyoxypropylenediamine x is about 2.6.

6. The product of claim 1 wherein in the polyoxypropylenediamine x is about 5.6.

7. The product of claim 1 wherein in the polyoxypropylenediamine x is about 33.1.

8. A process for preparing a liquid hydroxyurethane product having cyclocarbonate end groups which comprises reacting a bis-carbonate of a bis-glycidyl ether of the formula:

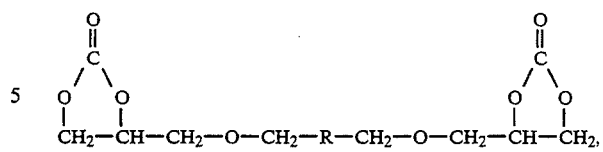

wherein R is selected from the group consisting of:

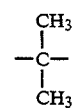

and

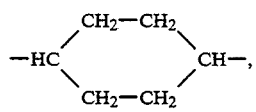

with a polyoxyalkylenediamine and wherein the molar ratio of the bis-carbonate of the bis-glycidyl ether reacted with the polyoxyalkylenediamine ranges from 5.0:1 to about 2.0:1 and wherein the polyoxyalkylenediamine is a polyoxypropylenediamine having the formula:

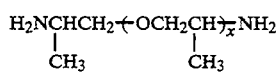

where x ranges from 2 to about 60.

9. The process of claim 8 wherein the reaction is conducted at a temperature ranging from ambient to about 250° C. and at a pressure ranging from atmospheric up to about 3000 psig.

10. The process of claim 8 wherein R is

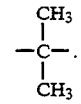

11. The process of claim 8 wherein R is:

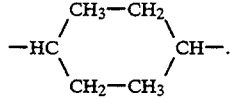

12. The process of claim 8 wherein in the polyoxypropylenediamine x is about 2.6.

13. The process of claim 8 wherein in the polyoxypropylenediamine x is about 5.6.

14. The process of claim 8 wherein in the polyoxypropylenediamine x is about 33.1.

* * * * *